US010138202B2

(12) United States Patent
Broell et al.

(10) Patent No.: US 10,138,202 B2
(45) Date of Patent: Nov. 27, 2018

(54) PROCESS FOR PREPARING N-ALKYL(METH)ACRYLAMIDES

(71) Applicant: Evonik Roehm GmbH, Darmstadt (DE)

(72) Inventors: Dirk Broell, Langen (DE); Benedikt Laux, Monzernheim (DE); Christian Maul, Neustadt a. d. W. (DE); Patrick Peter, Darmstadt (DE); Claus Zimmer, Worms (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 14/351,981

(22) PCT Filed: Nov. 20, 2012

(86) PCT No.: PCT/EP2012/073115
§ 371 (c)(1),
(2) Date: Apr. 15, 2014

(87) PCT Pub. No.: WO2013/092076
PCT Pub. Date: Jun. 27, 2013

(65) Prior Publication Data
US 2014/0288330 A1  Sep. 25, 2014

(30) Foreign Application Priority Data
Dec. 21, 2011  (DE) .................. 10 2011 089 363

(51) Int. Cl.
C07C 231/02 (2006.01)
C07C 231/24 (2006.01)

(52) U.S. Cl.
CPC .......... C07C 231/02 (2013.01); C07C 231/24 (2013.01)

(58) Field of Classification Search
CPC ..................... C07C 231/02; C07C 231/24
USPC ................................... 564/143, 144
See application file for complete search history.

(56) References Cited

U.S. PATENT DOCUMENTS

| 4,657,741 A * | 4/1987 | Vogl .................. B01J 8/067 165/159 |
| 5,302,754 A * | 4/1994 | Ibi .................. C07C 231/24 564/206 |
| 2010/0048951 A1 | 2/2010 | Morris |
| 2011/0218312 A1* | 9/2011 | Knebel et al. ............. 526/303.1 |

FOREIGN PATENT DOCUMENTS

| CN | 102131768 | 7/2011 |
| CN | 102197018 | 9/2011 |
| JP | 2006-176455 | 7/2006 |
| JP | 2007-230966 | 9/2007 |
| SU | 456408 A3 | 1/1975 |
| WO | 2010 021956 | 2/2010 |
| WO | WO 2010/021956 | 2/2010 |
| WO | 2010 072480 | 7/2010 |
| WO | WO 2010-126086 | 11/2010 |

OTHER PUBLICATIONS

International Search Report dated Jan. 21, 2013 in PCT/EP12/073115 Filed Nov. 20, 2012.
Office Action in Japanese Application No. 2014-547803, dated Jul. 19, 2016. (w/English Translation).

* cited by examiner

Primary Examiner — Pancham Bakshi
Assistant Examiner — Mark R Luderer
(74) Attorney, Agent, or Firm — Grüneberg and Myers PLLC

(57) ABSTRACT

The invention relates to a process for preparing N-alkyl (meth)acrylamides by reacting (meth)acrylic anhydride with corresponding alkylamines.

10 Claims, 1 Drawing Sheet

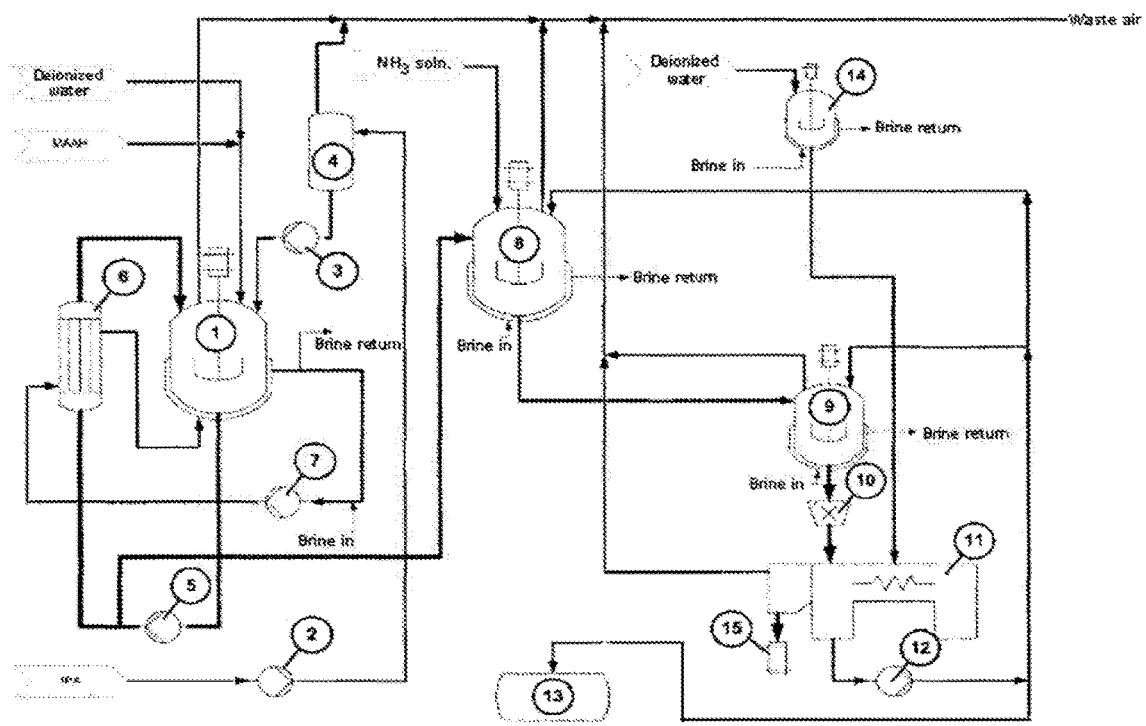

PROCESS FOR PREPARING N-ALKYL(METH)ACRYLAMIDES

FIELD OF THE INVENTION

The invention relates to a process for preparing N-alkyl (meth)acrylamides by reacting (meth)acrylic anhydride with corresponding alkylamines.

DISCUSSION OF THE BACKGROUND

The preparation of N-alkyl(meth)acrylamides is known. The Ritter reaction has for a long time been employed for preparing amides from nitriles and substrates which can form carbenium ions, e.g. tertiary or secondary alcohols, in the presence of strong mineral acids. DE 3131096 utilizes this process. A disadvantage is that the acid, which also functions as solvent, has to be neutralized and large amounts of salts are thus obtained. Furthermore, the product contains interfering impurities such as methacrylamide.

DE 4027843 describes a continuous process for preparing N-substituted (meth)acrylamides by transesterification of alkyl esters of (meth)acrylic acid with aliphatic and aromatic amines. Although the reaction makes do without a catalyst, it is carried out under severe conditions at >150° and a pressure of about 160 bar.

The process claimed in EP 2358664 for preparing N-isopropylmethacrylamide by reacting methacrylic anhydride with isopropylamine requires, in the preferred variant, the presence of an inert organic solvent, which is associated with a purification requirement for recycling. In the solvent-free variant, large quantities of heat are evolved and can lead to discoloration of the product.

WO 2010/021956 discloses the preparation of N-alkyl (alkyl)acrylamides, likewise from the corresponding acid anhydride and alkylamine. The addition of the anhydride to the initially charged amine is claimed here. This process variant is likewise associated with strong evolution of heat, which can cause the discoloration cited above. In addition, there is only a narrow process window in which no severely troublesome lump formation occurs.

It is therefore an object of the present invention to provide an alternative process for preparing N-alkyl(meth)acrylamides which does not have the abovementioned disadvantages and, in particular, produces products in high yield and purity, with these being obtained under moderate reaction conditions, preferably from 1 to 10 bar and from 20 to 100° C., and in a problem-free manner.

These objects and also further objects which are not set forth in detail but can readily be deduced or derived from the introductory presentation of the prior art are achieved by a process having the features of claim 1. Advantageous modifications of the process of the invention are protected in the claims which refer back to claim 1.

BRIEF DESCRIPTION OF THE DRAWING

The FIGURE shows an embodiment of the preparation of N-isopropylmethacrylamide (NIPMAA).

DETAILED DESCRIPTION OF THE INVENTION

The invention provides a process for preparing N-alkyl (meth)acrylamides of the general formula (1),

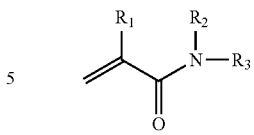

where $R_1$ is H or a $CH_3$ group, $R_2$ and $R_3$ are hydrogen or a linear, branched or cyclic alkyl radical or aryl radical having from 1 to 12 carbon atoms. The reaction is carried out by reacting initially charged (meth)acrylic anhydride with an aqueous solution of an alkylamine of the formula (2), $$R_2R_3NH \qquad (2)$$

where $R_2$ and $R_3$ are as defined above, and separating off the amide formed. The expression (meth)acrylic anhydride refers to both methacrylic anhydride and acrylic anhydride. It has surprisingly been found that this procedure does not lead, in contrast to WO 2010/021956, to uncontrolled precipitates in the form of lumps or deposits on the reactor wall at any point in time.

Possible primary amines are primary, optionally substituted aliphatic amines, for example methylamine, ethylamine, propylamine, butylamine, pentylamine, hexylamine, heptylamine, octylamine, dodecylamine, isopropylamine, isobutylamine and benzylamine and also allylamine and ammonia. Furthermore, it is possible to use primary cycloaliphatic amines, for example cyclopropylamine, cyclobutylamine, cyclopentylamine and cyclohexylamine. As primary aromatic amines, it is possible to use aniline, the isomeric aminotoluenes, either individually or in mixtures, and the isomeric xylidines, either individually or in mixtures. These compounds can optionally be substituted by one or more halogens.

As secondary amines, it is likewise possible to use aliphatic, cycloaliphatic or aromatic amines which can optionally be substituted by one or more halogens. Particular preference is given to dimethylamine, diethylamine, methylethylamine, dibutylamine, dibenzylamine, morpholine and optionally substituted piperidines.

Since polymerizable compounds are prepared here, the reaction has to be carried out in the presence of polymerization inhibitors. The reaction can be carried out under atmospheric oxygen or protective gas. In the first case, the appropriate explosion protection limits have to be adhered to and inhibitors which act under atmospheric oxygen have to be used. Since the process of the invention preferably proceeds under protective gas, particularly preferably under nitrogen, only polymerization inhibitors which also act with exclusion of oxygen can be used in this case. As such polymerization inhibitors, 4-hydroxy-2,2,6,6-tetramethylpiperidin-1-oxyl, N,N'-diphenyl-p-phenylenediamine, triazines, phenazines, phenothiazines, methylene blue or sterically hindered phenols, for example, are widely known in the art. These compounds can be used individually or in the form of mixtures and are generally commercially available. For further details, reference may be made to the relevant technical literature, in particular Römpp-Lexikon Chemie; editor: J. Falbe, M. Regitz; Stuttgart, New York; 10$^{th}$ edition (1996); keyword "Antioxidantien" [Antioxidants] and the literature references cited there. Particular preference is given to 4-hydroxy-2,2,6,6-tetramethylpiperidin-1-oxyl or 4-methyl-2,6-di-tert-butylphenol, either individually or in mixtures. Customary concentrations used here are in the range from 1 to 2000 ppm, preferably from 20 to 200 ppm, particularly preferably from 40 to 80 ppm, based on the total reaction mixture.

In the process of the invention, the (meth)acrylic anhydride is placed in a suitable stirred reactor, optionally with external heat exchanger and circulation pump, admixed with polymerization inhibitors and cooled to below 30° C., preferably to from 10 to −5° C. The reactor is flushed with protective gas, preferably nitrogen. The aqueous solution of the amine is provided in a reservoir and likewise cooled to below 30° C., preferably to from 10 to −5° C. The concentration of the amine in the aqueous solution can be from 50 to 90%, preferably from 60 to 80%, particularly preferably from 65 to 75%. The molar ratio of (meth)acrylic anhydride to amine is in the range from 0.8:1.2 to 1.2:0.8, preferably 1:1. The addition of the aqueous amine solution to the (meth)acrylic anhydride is carried out at such a rate that the initial reaction temperature of the exothermic reaction does not exceed 25° C., preferably does not exceed 15° C. The further addition is carried out in such a way that the internal temperature in the reactor increases, as a function of the conversion, to a maximum value of 40° C. and the temperature of the cooling liquid used for cooling the reaction vessel is not below the crystallization temperature of the amine formed in the reaction solution at any point in time. The reactor pressure should be kept in the range from 0.5 to 6 bar, preferably from 0 to 1 bar.

For neutralization, the reaction solution is transferred to a further vessel, preferably equipped with a stirrer. Neutralization is carried out using alkaline solutions, preferably NaOH or KOH solution, particularly preferably ammonia solution. The reaction solution can optionally be diluted with water or the mother liquor from the centrifuge beforehand. Before commencement of neutralization, the reaction solution is cooled to below 20° C., preferably to below 15° C. The alkaline solution has to be introduced in such a way that the temperature does not exceed 60° C., preferably 50° C., at any point in time. After neutralization, the mixture with the precipitated product crystals is cooled to below 10° C., preferably to 5° C., particularly preferably to −5° C.

To isolate the solid from the neutralized mixture, it is possible to use solid/liquid separation methods with which a person skilled in the art will be familiar, e.g. filtration or centrifugation. In the process of the invention, preference is given to centrifugation with an optional preceding milling step. To mill the crystal suspension, it is possible to use, for example, suspension mills or wet mills (e.g. from Fryma). Centrifugation is carried out at temperatures below 10° C., preferably below 5° C., in particular below −5° C. The yield of N-akyl(meth)acrylamide is normally in the range from 80 to 85%, based on N-alkyl(meth)acrylic anhydride.

The following example illustrates the process of the invention, but does not restrict it in any way.

EXAMPLES

EXAMPLE 1

The preparation of N-isopropylmethacrylamide (NIPMAA) is carried out as shown in the FIGURE. 800 kg of methacrylic anhydride are placed in the stirred reactor (1) and, after mixing with 135 g of 4-methyl-2,6-di-tert-butylphenol and 115 g of 4-hydroxy-2,2,6,6-tetramethylpiperidin-1-oxyl, precooled to −5° C. The reactor (1) is flushed with nitrogen. The pressure regulator is set to 1.3 bar. 437 kg of 70% strength isopropylamine solution are pumped by means of the pump (2) into the reservoir (4) which can be cooled. The isopropylamine is introduced into the reactor (1) via the metering pump (3) in such a way that the reaction temperature is in the range from −5 to 40° C. during the reaction. The contents of the reactor are circulated via the heat exchanger (6) by means of the pump (5) during the reaction. The heat of reaction is removed by brine cooling (7) of the reactor (1) and the heat exchanger (6). After all the isopropylamine has been added, an after-reaction is carried out for 15 minutes at 20-40° C., preferably at 35-40° C. The slurry of NIPMAA in methacrylic acid formed after the reaction is diluted with 1100 kg of deionized water (demineralized water) to reduce the viscosity. The diluted mixture is transferred by means of the pump (5) to the stirred vessel (8) and neutralized by means of 355 kg of 25% strength ammonia solution while stirring. The major part of the NIPMAA precipitates in the neutralization, while the ammonium methacrylate formed remains in solution. To separate off the NIPMAA, the suspension is drained via the buffer reservoir (9) which serves for buffering the crystal slurry. The buffer reservoir (9) is cooled (to max. −5° C.). The buffered suspension is introduced via the mill (10) into the centrifuge (11). Cold deionized water (~5° C.) which is used for washing the crystals in the centrifuge (11) in order to obtain the necessary purity is provided via the deionized water container (14). The aqueous mother liquor, which contains mainly ammonium methacrylate in addition to NIPMAA, is pumped by means of the pump (12) back into (8) or (9). At the end of the centrifugation, all of the mother liquor is collected in the vessel (13). The yield of NIPMAA in the NIPMAA reservoir (15) is 84%, based on methacrylic anhydride.

If the mixture in the reaction phase is cooled too much, crystals and deposits are formed on the reactor walls and in the heat exchanger, after which the reaction has to be stopped. If, on the other hand, the reaction temperature exceeds the limits indicated, quality-reducing discoloration and decreases in yield occur. Similar problems arise when the appropriate amine is initially charged and (meth)acrylic anhydride is added thereto.

The N-alkyl(meth)acrylamides prepared by the process of the invention can be converted in a manner known per se into polymers and copolymers for use in a wide variety of applications.

| List of reference numerals: | |
| --- | --- |
| Number | Name |
| 1 | Stirred reactor |
| 2 | Pump |
| 3 | Metering pump |
| 4 | Reservoir vessel |
| 5 | Pump |
| 6 | Heat exchanger |
| 7 | Brine cooling |
| 8 | Stirred vessel |
| 9 | Buffer reservoir |
| 10 | Mill |
| 11 | Centrifuge |
| 12 | Pump |
| 13 | Vessel |
| 14 | Deionized water container |
| 15 | NIPMAA reservoir |

The invention claimed is:

1. A process for preparing an N-alkyl(meth)acrylamide of formula (1), the process comprising:
charging (meth)acrylic anhydride in a reaction vessel;
reacting (meth)acrylic anhydride with an aqueous solution of an alkylamine of formula (2) at a temperature of from −5° C. to 40° C. and a pressure of from 0.5 to 6 bar, thereby obtaining the N-alkyl(meth)acrylamide in a reaction solution, wherein the initial reaction temperature does not exceed 25° C.;

cooling the reaction vessel to a temperature above a crystallization temperature of the N-alkyl(meth)acrylamide in the reaction solution; and separating the N-alkyl(meth)acrylamide:

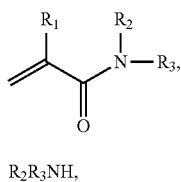

(1)

$R_2R_3NH$, (2)

where $R_1$ is H or a $CH_3$ group, and $R_2$ and $R_3$ are hydrogen or a linear, branched or cyclic alkyl radical or aryl radical comprising from 1 to 12 carbon atoms, wherein uncontrolled precipitates in the form of lumps or deposits do not form on the walls of the reaction vessel, wherein the alkylamine is precooled to below 30° C. before said reacting, and wherein a concentration of the alkylamine in the aqueous solution is 50-90%.

2. The process according to claim 1, further comprising:

diluting the reaction solution comprising the N-alkyl(meth)acrylamide and (meth)acrylic acid with water, optionally with a centrifuge mother liquor, subsequently neutralizing the reaction solution using an alkaline solution, thereby obtaining a precipitated N-alkyl(meth)acrylamide, and separating the precipitated N-alkyl(meth)acrylamide.

3. The process according to claim 2, wherein said reacting and said neutralizing are each carried out in a separate vessel.

4. The process according to claim 1, wherein said reacting is carried out in the presence of water-soluble polymerization inhibitors which act under inert gas.

5. The process according to claim 1, further comprising:

milling a product crystal slurry obtained after said reacting in a mill before said separating in a centrifuge.

6. The process according to claim 1, wherein the reaction vessel is equipped with an external heat exchanger and a circulation pump.

7. The process according to claim 1, wherein the alkylamine is precooled to a temperature of −5 to 10° C. before said reacting.

8. The process according to claim 1, wherein the concentration of the alkylamine in the aqueous solution is 60-80%.

9. The process according to claim 1, wherein the concentration of the alkylamine in the aqueous solution is 65-75%.

10. A process for preparing an N-alkyl(meth)acrylamide of formula (1), the process comprising:

charging (meth)acrylic anhydride in a reaction vessel;

reacting (meth)acrylic anhydride with an aqueous solution of an alkylamine of formula (2) at a temperature of from −5° C. to 40° C. and a pressure of from 0.5 to 6 bar, thereby obtaining the N-alkyl(meth)acrylamide in a reaction solution, wherein the initial reaction temperature does not exceed 25° C.;

cooling the reaction vessel to a temperature above a crystallization temperature of the N-alkyl(meth)acrylamide in the reaction solution; and separating the N-alkyl(meth)acrylamide:

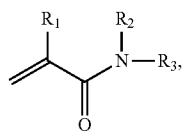

(1)

$R_2R_3NH$, (2)

where $R_1$ is H or a $CH_3$ group, and $R_2$ and $R_3$ are hydrogen or a linear, branched or cyclic alkyl radical or aryl radical comprising from 1 to 12 carbon atoms, wherein uncontrolled precipitates in the form of lumps or deposits do not form on the walls of the reaction vessel, wherein the aqueous solution of the alkylamine is added to the reaction vessel after the (meth)acrylic anhydride has been charged in the reaction vessel, wherein the alkylamine is precooled to below 30° C. before said reacting, and wherein a concentration of the alkylamine in the aqueous solution is 50-90%.

* * * * *